United States Patent [19]
Winslow et al.

[11] Patent Number: 5,885,299
[45] Date of Patent: *Mar. 23, 1999

[54] APPARATUS AND METHOD FOR IMPLANT INSERTION

[75] Inventors: Charles J. Winslow, Walnut Creek; Steven T. Mitchell, Pleasant Hill, both of Calif.

[73] Assignee: Surgical Dynamics, Inc., Norwalk, Conn.

[*] Notice: This patent issued on a continued prosecution application filed under 37 CFR 1.53(d), and is subject to the twenty year patent term provisions of 35 U.S.C. 154(a)(2).

[21] Appl. No.: 616,120

[22] Filed: Mar. 14, 1996

Related U.S. Application Data

[63] Continuation-in-part of Ser. No. 354,364, Dec. 12, 1994, abandoned, which is a continuation-in-part of Ser. No. 306,879, Sep. 15, 1994, abandoned.

[51] Int. Cl.⁶ ................................................ A61B 17/56
[52] U.S. Cl. ................................................ 606/99; 606/61
[58] Field of Search ........................... 606/61, 73, 91, 606/99, 104, 72, 60, 86; 623/17

[56] References Cited

U.S. PATENT DOCUMENTS

| | | |
|---|---|---|
| Re. 31,628 | 7/1984 | Allgower et al. . |
| Re. 31,865 | 4/1985 | Roux . |
| 2,537,070 | 1/1951 | Longfellow . |
| 3,112,743 | 12/1963 | Cochran et al. . |
| 3,298,372 | 1/1967 | Feinberg . |
| 3,426,364 | 2/1969 | Lumb . |

(List continued on next page.)

FOREIGN PATENT DOCUMENTS

| | | |
|---|---|---|
| 2015507 | 12/1974 | Canada . |
| 0073177 | 3/1983 | European Pat. Off. . |
| 0260044 | 3/1988 | European Pat. Off. . |
| 0260222 | 3/1988 | European Pat. Off. . |
| 0269175 | 6/1988 | European Pat. Off. . |
| 0269176 | 6/1988 | European Pat. Off. . |

(List continued on next page.)

OTHER PUBLICATIONS

Kaneda et al., "Spinal Instrumentation Surgery in Lumbar and Lumbosacral Spine" The Improvement of Medicine, vol. 147, No. 14, Dec. 31, 1988.

Hiroshi Yamamoto, "Spinal Instrumentation for Lumbar Spine — Segmental Transverse Wiring for Spondylolysis and Pedicular Screw–Spinal Plate for Spondylolisthesis," The Improvement of Medicine, vol. 145, No. 1, Apr. 2, 1988.

(List continued on next page.)

*Primary Examiner*—Guy V. Tucker

[57] ABSTRACT

Apparatus for and methods of inserting implants are disclosed wherein the apparatus includes a handle portion and a body portion attached to the handle portion and defining a longitudinal axis. The body portion includes an outer tubular member fixed relative to the handle portion for rotation therewith about the longitudinal axis. The outer tube member has first implant engaging structure adjacent a distal end. An inner tubular member is disposed at least partially within the outer tubular member and is mounted for longitudinal motion relative to the outer tubular member. Second implant engaging structure is positioned adjacent a distal end of the inner tubular member. The body portion further includes an inner shaft, coaxially mounted at least partially within the inner tubular member for independent rotation relative to the inner and outer tubular members, the inner shaft having third implant engaging structure adjacent a distal end. In a method for inserting an implant having a hollow portion with a closed distal end and a removable cap, the first, second and third implant engaging structures are attached to the implant with at least one of the engaging structure attached to the removable cap and another of the engaging structure attached to the hollow portion. The implant is preferably preloaded with bone chips and/or bone growth inducing substances prior to attachment. Thereafter, the preloaded implant is inserted into the desired surgical location.

28 Claims, 10 Drawing Sheets

U.S. PATENT DOCUMENTS

| | | |
|---|---|---|
| 3,486,505 | 12/1969 | Morrison . |
| 3,514,791 | 6/1970 | Sparks . |
| 3,625,198 | 12/1971 | Sparks . |
| 3,719,186 | 3/1973 | Merig, Jr. . |
| 3,720,959 | 3/1973 | Hahn . |
| 3,783,860 | 1/1974 | Burstein et al. . |
| 3,848,601 | 11/1974 | Ma et al. . |
| 3,849,805 | 11/1974 | Leake et al. . |
| 3,852,045 | 12/1974 | Wheeler et al. . |
| 3,855,638 | 12/1974 | Pilliar . |
| 3,867,728 | 2/1975 | Stubstad et al. . |
| 3,871,031 | 3/1975 | Boutin . |
| 3,905,047 | 9/1975 | Long . |
| 3,906,550 | 9/1975 | Rostoker et al. . |
| 3,916,907 | 11/1975 | Peterson . |
| 3,986,212 | 10/1976 | Sauer . |
| 4,013,071 | 3/1977 | Rosenberg . |
| 4,016,651 | 4/1977 | Kawahara et al. . |
| 4,059,115 | 11/1977 | Jumashev et al. . |
| 4,086,701 | 5/1978 | Kawahara et al. . |
| 4,124,026 | 11/1978 | Berner et al. . |
| 4,177,524 | 12/1979 | Grell et al. . |
| 4,180,910 | 1/1980 | Straumann et al. . |
| 4,185,383 | 1/1980 | Heimke et al. . |
| 4,259,072 | 3/1981 | Hirabayashi et al. . |
| 4,289,123 | 9/1981 | Dunn . |
| 4,309,777 | 1/1982 | Patil . |
| 4,328,593 | 5/1982 | Sutter et al. . |
| 4,349,921 | 9/1982 | Kuntz . |
| 4,401,112 | 8/1983 | Rezaian . |
| 4,406,623 | 9/1983 | Grafelmann et al. . |
| 4,468,200 | 8/1984 | Münch . |
| 4,484,570 | 11/1984 | Sutter et al. . |
| 4,492,226 | 1/1985 | Belykh et al. . |
| 4,493,317 | 1/1985 | Klaue . |
| 4,501,269 | 2/1985 | Bagby . |
| 4,511,336 | 4/1985 | Hidaka et al. . |
| 4,513,744 | 4/1985 | Klaue . |
| 4,522,200 | 6/1985 | Stednitz . |
| 4,525,145 | 6/1985 | Scheicher et al. . |
| 4,537,185 | 8/1985 | Stednitz . |
| 4,545,374 | 10/1985 | Jacobson . |
| 4,549,319 | 10/1985 | Meyer . |
| 4,553,273 | 11/1985 | Wu . |
| 4,569,338 | 2/1986 | Edwards . |
| 4,573,448 | 3/1986 | Kambin . |
| 4,599,084 | 7/1986 | Nashef . |
| 4,599,086 | 7/1986 | Doty . |
| 4,611,581 | 9/1986 | Steffee . |
| 4,636,217 | 1/1987 | Ogilvie et al. . |
| 4,653,481 | 3/1987 | Howland et al. . |
| 4,653,486 | 3/1987 | Coker . |
| 4,655,199 | 4/1987 | Steffee . |
| 4,657,550 | 4/1987 | Daher . |
| 4,662,891 | 5/1987 | Noiles . |
| 4,673,409 | 6/1987 | Van Kampen . |
| 4,677,972 | 7/1987 | Tornier . |
| 4,714,469 | 12/1987 | Kenna . |
| 4,721,103 | 1/1988 | Freedland . |
| 4,725,280 | 2/1988 | Laure . |
| 4,736,738 | 4/1988 | Lipovsek . |
| 4,743,256 | 5/1988 | Brantigan . |
| 4,743,260 | 5/1988 | Burton . |
| 4,759,768 | 7/1988 | Hermann et al. . |
| 4,769,041 | 9/1988 | Morscher . |
| 4,772,287 | 9/1988 | Ray . |
| 4,790,297 | 12/1988 | Luque . |
| 4,790,303 | 12/1988 | Steffee . |
| 4,802,468 | 2/1989 | Powlan . |
| 4,820,305 | 4/1989 | Harms et al. . |
| 4,834,757 | 5/1989 | Brantigan . |
| 4,842,517 | 6/1989 | Kawahara et al. . |
| 4,863,430 | 9/1989 | Klyce et al. . |
| 4,863,474 | 9/1989 | Brown et al. . |
| 4,877,020 | 10/1989 | Vich . |
| 4,878,915 | 11/1989 | Brantigan . |
| 4,904,260 | 2/1990 | Ray . |
| 4,904,261 | 2/1990 | Dove et al. . |
| 4,927,421 | 5/1990 | Goble et al. . |
| 4,936,848 | 6/1990 | Bagby . |
| 4,936,851 | 6/1990 | Fox et al. . |
| 4,950,270 | 8/1990 | Bowman et al. . |
| 4,961,740 | 10/1990 | Ray et al. . |
| 5,015,247 | 5/1991 | Michelson . |
| 5,015,255 | 5/1991 | Kuslich . |
| 5,026,373 | 6/1991 | Ray et al. . |
| 5,055,104 | 10/1991 | Ray . |
| 5,059,193 | 10/1991 | Kuslich . |
| 5,062,845 | 11/1991 | Kuslich et al. . |
| 5,139,499 | 8/1992 | Small et al. . |
| 5,147,402 | 9/1992 | Bohler et al. . |
| 5,195,541 | 3/1993 | Obenchain . |
| 5,263,953 | 11/1993 | Bagby . |
| 5,300,076 | 4/1994 | Leriche . |
| 5,313,962 | 5/1994 | Obenchain . |
| 5,354,302 | 10/1994 | Ko . |
| 5,357,983 | 10/1994 | Mathews . |
| 5,358,511 | 10/1994 | Gatturna et al. . |
| 5,400,805 | 3/1995 | Warren . |
| 5,423,817 | 6/1995 | Lin . |
| 5,425,772 | 6/1995 | Brantigon . |
| 5,425,773 | 6/1995 | Boyd et al. . |
| 5,439,464 | 8/1995 | Shapiro . |
| 5,445,639 | 8/1995 | Kuslich et al. . |
| 5,454,811 | 10/1995 | Huebner . |
| 5,458,638 | 10/1995 | Kuslich et al. . |
| 5,470,334 | 11/1995 | Ross et al. . |
| 5,480,403 | 1/1996 | Lee et al. . |
| 5,484,437 | 1/1996 | Michelson . |
| 5,489,308 | 2/1996 | Kuslich et al. . |

FOREIGN PATENT DOCUMENTS

| | | |
|---|---|---|
| 2 295 729 | 12/1974 | France . |
| 1 961 531 | 7/1970 | Germany . |
| 3505567 | 6/1986 | Germany . |
| 56-34731 | 8/1981 | Japan . |
| 57-29348 | 2/1982 | Japan . |
| 58-78653 | 5/1983 | Japan . |
| 61-135652 | 6/1986 | Japan . |
| 62-164458 | 7/1987 | Japan . |
| 63-43654 | 2/1988 | Japan . |
| 63-158045 | 7/1988 | Japan . |
| 1-502402 | 8/1989 | Japan . |
| 1-314560 | 12/1989 | Japan . |
| 283078 | 2/1985 | Spain . |
| WO/86/03666 | 7/1986 | WIPO . |
| 8803781 | 6/1988 | WIPO . |
| WO/89/09035 | 10/1989 | WIPO . |
| 9000037 | 1/1990 | WIPO . |

OTHER PUBLICATIONS

Shibata et al., "A New Conrivance of Anterior Spinal Fusion in Cervical Spine", Orhopaedic and Traumatic Surgery, vol. 35, No. 3, pp. 811–813, 1987.

Haruo Tsuji, "Anterior Body Fusion of Lumbar Spine Hernia", Operation, vol. 41, No. 11, pp. 1803–1811, 1987.

Hirotugu Oda et al., "Osteoplastic–Hemi/Bilater Partial Laminectomy of Lumbar Spinal Hernia", Operation, vol. 41, No. 11, pp. 1785–1791, 1987.

Teiji Yano et al., "Treatment of Spondylolisthesis by Posterior Fusion with Bone Grafting to Neural Arch Defect", Clinical Orthopaedic Surgery, vol. 17, No. 4, pp. 394–399, 1982.

Toshihiko Yamane, et al., "A case Report of Multiple Lumbar Spondylolyses with Spondylolisthesis", Clinical Orthopaedic Surgery, vol. 23, No. 3, pp. 311–314, 1988.

M. Maeshiro, et al., "Posterior Fracture Dislocation of the Thoracic Spine: Two Cases Report", Orthopaedic Surgery, vol. 39, No. 9, pp. 1373–1377, 1988–1989.

Kunio Takaoka, "Clinical Application of Ceramic Implants in Orthopaedic Surgery", Medicina philosophica, vol. 4, No. 7, pp. 546–552, 1985.

Y. Yamano et al., "Anterior Body Fusion of Lumbar Degenerative Spondylolisthese", Journal of the Western Japanese Research Society For Spine, vol. 13, pp. 46–50.

"Dual Chisel and Its Bank Bones (Skimud Subkortikate Bones) for Posterior Lumbar Interbody Fusion — In Order to Simplify and Regularize the Surgical Procedure", Orthopaedic Surgery, vol. 11, pp. 150–153, (Author Unknown).

"Vertebral Body Distraction System (Caspar)", Orthopaedic Surgery, vol. 11, pp. 135–139, (Author Unknown).

Takayoshi Ueda et al., "Instrumentation Surgery of Lumbar Interbody Fusion", Central Japan Journal of Orthopaedic and Traumatic Surgery, pp. 87–89.

Haruo Tsuji et al., "Development and Clinical Application of Artificial Intervertebral Disc for Cervical Disc Lesions", Central Japan Journal of Orthopaedic & Traumatic Surgery, pp. 1505–1506.

Benjamin R. Witberger, M.D., "Intervertebral Body Fusion By The Use Of Posterior Bone Dowel", Clinical Orthopaedics, 35:69–79, 1964.

"Gewebsreaktion auf ein Titan–Hohlzylinderimpantat mit Titan–Spritzschichtoberfläche", by A. Schroeder, O. Pohler and F. Sutter, Separatdruck aus: Schweiz. Mschr. Zahnheilk vol. 86, No. 7, pp. 713–727, 1976.

"Osseointegrated Titanium Implants, Requirements for Ensuring a Long–Lasting, Direct Bone–to–Implant Anchorage in Man", by T. Albrektsson et al., Acta Orthop. Scand., vol. 52, pp. 155–170, 1981.

"The Reactions of Bone, Connective Tissue, and Ephithelium to Endosteal Implants With Titanium–Sprayed Surfaces", by Andre Schroeder et al., J. max.–fac. Surg. 9, pp. 15–25, 1981.

"Neue Rekonstruktionsmöglichkeiten bei Unterkiefrdefekten nach Tummorresektion", by J. Raveh et al., Separatdruck aus: Schweiz. Mschr. Zahnheilk vol. 91, Nr. 11, pp. 899–920, 1981.

"Cementless Fixation of Polyethylene Acetabular Component in Total Hip Arthroplasty", by E. W. Morscher et al., Archives of Arthopaedic and Tumatic SUrgery, vol. 99, Issue 4, pp. 223–230, 1982.

"Neue Rekonstruktionsmöglichkeiten des Unterkiefers bei knöchernen Defekten nach Tumorresektionen", by J. Raueh et al., Chirurg, vol. 53, pp. 459–467, 1982.

"New Concepts in the Reconstruction of Mandibular Defects Following Tumor Resection", by. Y. Reveh, M.D., DMD, et al., J Oral Maxillofax Surg, vol. 41, Issue 1, pp. 3–16, Jan. 1983.

"Use of the Titanium Coated Hollow Screw and Reconstruction Plate System in Bridging Lower Jaw Defects", by J. Raveh, et al., J. Oral Maxillofac Surg., vol. 42, Issue 5, pp. 281–294, May 1984.

"Titanplasma–beschichtetes Holschrauben–und Rekonstruktions–platten–System (THRP) zur Überbrückung von Kieferdefekten", by F. Sutter et al., Chirurg, vol. 55, Issue 1, pp. 741–748, Nov. 1984.

"Titanplasma–beschichtetes Hohlschrauben–und Rekonstruktionsplatten–System (THRP) zur Überbrückrung von Kieferdefekten", by F. Sutter et al., Chirurg, vol. 56, Issue 5, pp. 337–344, May 1985.

"Anterior Cervical Interbody Fusion With Threaded Cylindrical Bone", by Jose M. Otero Vich, M.D., J. Neurosurg, vol. 63, pp. 750–753, Nov., 1985.

"Die vordere Verplattung der Halswirbelsäule mit dem Hohlschrauben–Plattensystem aus Titanium", by E. Morscher et al., Chirurg, vol. 57, Issue 11, pp. 702–707, 1986.

"Surgical Procedures for Reconstruction of the Lower Jaw Using the Titanium–Coated Hollow–Screw Reconstruction Plate System: Bridging of Defects", by J. Raveh et al., The Otolaryngologi Clinics of North America, vol. 20, No. 3, pp. 535–558, Aug., 1987.

"Titanium Coated Hollow Screw and Reconstruction Plate System For Bridging of Lower Jaw Defects: Biomechanical Aspects", by F. Sutter et al., Int. J. Oral Maxillofac. Surg., vol. 17, Issue 4, pp. 267–274, 1988.

Arthrodesis By The Distraction–Compression Method Using A Stainless Steel Implant, by George W. Bagby, M.D., M.S., Orthopedics, vol. 11, pp. 931–934, Jun. 1988.

Engineering and Design Aspects of the I.T.I. Hollow–Basket Implants, by F. Sutter, D.D.S., et al., Journal of Oral Implantology, pp. 535–551, 1983.

American Journal of Veterinarian Research, Author: Unknown, vol. 45, No. 1, Jan. 1984, pp. 195–199.

"Posterior Lumbar Interbody Fusion Made Simple", by G. M. Sava, Neurological Surgery Associates of Cincinnati, Inc., 2 pages, undated.

Surgical Titanium Mesh Ordering Information, DePuy Motech, Warsaw, Indiana, U.S.A., 2 pages, undated.

Cage CH — Lumbar spacing cages, Scient'x, Paris, France, 4 pages, undated.

"Basket Implant Facilitates Spinal Fusion", Orthopedics Today, vol. 7, No. 10, Oct. 1987, p. 4.

Norman W. Hoover, M.D., "Methods of Lumbar Fusion", The Journal of Bone and Joint Surgery, Jan. 1968, pp. 194–210.

Shun–Ichi Inque, M.D., Ph.D., et al., "Anterior Discectomy and Interbody Fusion for Lumbar Disc Herniation", Lumbar Disc Herniation, vol. 183, Mar. 1984, pp. 22–31.

A. Kumar, M.D., et al., "Interspace Distraction and Graft Subsidence After Anterior Lumbar Fusion With Femoral Strut Allograft", Spine vol. 18, No. 16, pp. 2392–2400, 1993.

Charles V. Burton, "Fusion: What It's Been and Where It's Going", The International Society for the Study of the Lumbar Spine, The Lumbar Spine, Chapter 23, pp. 998–1003.

Keith H. Bridwell, M.D., "Normal Sagittal Alignment", Federation of Spine Associations, Section IV — Scoliosis Research Society, Sagittal Spinal Balance –Symposium No. 1, Feb. 27, 1994.

Charles G. Hutter, "A Technique for Posterior Lumbar Interbody Fusion", Chapter 19, Lumbar Interbody Fusion, 1989, pp. 227–232.

S+G Implants, S+G Spongiosametall Lübeck, Blöcke Typ Waisbrod, 2 pages, Author and Date Unknown.

S+G Implants, S+G Cast Cancellous Metal, PLIF (Posterior Lumbar Interbody Fusion) with Cast Cancellous Metal Mould (CCMM), 4 pages, Author and Date uknown.

Cage, CR, Cerivical Spacing Cages, Cages Intersomatiques Cervicales, Scient'x, Paris, 1 page.

Actualités Vertébrales, La Hernie Discale Cervicale, No. 2, Avril 994, 11 pages.

Cage CH — Lumbar spacing cages, Scient'x, Paris, France, 4 pages undated.

FIG_3

FIG_4

FIG. 5

FIG_12

APPARATUS AND METHOD FOR IMPLANT INSERTION

This application is a continuation-in-part of U.S. application Ser. No. 08/354,364, filed on Dec. 12, 1994, abandoned, which is a continuation-in-part of U.S. application Ser. No. 08/306,879, filed on Sep. 15, 1994, now abandoned. The contents of these applications are incorporated herein by reference.

BACKGROUND

1. Technical Field

This disclosure relates generally to apparatus and methods for implant insertion. More particularly, to apparatus and methods for insertion of implants to facilitate fusion of adjacent bony structure.

2. Background of the Related Art

A large number of orthopedic procedures involve the insertion of either natural or prosthetic implants into bone or associated tissues. These procedures include, for example, ligament repair, joint repair or replacement, non-union fractures, facial reconstruction, spinal stabilization and spinal fusion. In a typical procedure, an insert, dowel or screw is inserted into a prepared bore formed in the bone or tissues to facilitate repair and healing. See, for example, U.S. Pat. No. : 5,470,334 to Ross et al.; U.S. Pat. No. 5,454,811 to Huebner; U.S. Pat. No. 5,480,403 to Lee et al.; U.S. Pat. No. 5,40,805 to Warren; U.S. Pat. No. 5,358,511 to Gatturna et al.; and U.S. Pat. No. 4,877,020 to Vich.

Some implants are particularly configured with cavities and bores to facilitate bony ingrowth and enhance anchoring of the implant at the insertion site. See, for example, U.S. Pat. No. : 4,328,593 to Sutter et al.; U.S. Pat. No. 4,936,851 to Fox et al.; and U.S. Pat. No. 4,878,915 to Brantigan. Implants in the form of fusion cages having internal cavities to receive bone growth stimulation materials such as bone chips and fragments are disclosed, for example, in U.S. Pat. No. : 4,501,269 to Bagby; U.S. Pat. No. 4,961,740 to Ray et al.; U.S. Pat. No. 5,015,247 to Michaelson; and U.S. Pat. No. 5,489,307 to Kuslich et al. These types of implants are particularly well suited for intervertebral spinal fusion procedures necessitated by injury, disease or some degenerative disorder of the spinal disc. Subsequently, there may be progressive degeneration leading to mechanical instability between adjacent vertebrae necessitating direct fusion of the vertebrae while maintaining a pre-defined intervertebral space. This fusion may be accomplished by the insertion of one or more of the specialized implants as discussed above and also discussed in commonly assigned U.S. Pat. No. 5,026,373, incorporated herein by reference.

Both anterior (transabdominal) and posterior surgical approaches are used for interbody fusions of the lumbar spine. Fusions in the cervical area of the spine are primarily done using an anterior approach. Typically, an implant such as a plug, dowel, prosthesis or cage is inserted into a preformed cavity inside the interbody, interdiscal space. Since it is desirable in these procedures to promote a "bone to bone" bridge, connective tissue and at least a portion of the discal tissue is removed. Preferably, relatively deep cuts are made in the adjacent bones in order to penetrate into the softer, more vascularized cancellous region to facilitate bone growth across the implant.

When installing these specialized implants, an insertion tool is used to position the implant in the desired intervertebral location. See, for example, U.S. Pat. No.: 3,848,601 to Ma et al.; U.S. Pat. No. 4,501,269 to Bagby; U.S. Pat. No. 4,877,020 to Vich; and U.S. Pat. No. 4,878,915 to Brantigan. Once in position, the insertion tool is removed and, where the implant structure permits, bone chips or other bone growth inducing substances are packed into the implant in vivo. Subsequently, an end cap or other sealing structure is positioned to close the implant. See, for example, commonly assigned U.S. Pat. No. 4,961,740 to Ray et al. incorporated herein by reference.

Typical insertion tools use either a single implant engagement structure or, at most, two implant engagement structures to facilitate positioning of the implant. For example, in U.S. Pat. No. 4,501,269 to Bagby, prongs are used to engage the implant. In U.S. Pat. No. 4,878,915 to Brantigan and U.S. Pat. No. 5,015,247 to Michaelson, a threaded rod and slot are used to engage the implant In U.S. Pat. No. : 4,961,740 to Ray et al.; U.S. Pat. Nos. 5,489,308 and 5,489,307, both to Kuslich et al.; and U.S. Pat. No. 4,936,838 to Bagby, a single central shaft is used. In all of these insertion tools, no structure is provided to permit the insertion tool to attach to an outer peripheral portion of the implant, either in vitro or in vivo. Further, these tools do not provide structure which separately engages both the implant and the implant closure, e.g. an end cap.

Accordingly, a need exists for an insertion tool which is capable of either inserting an implant preloaded with bone chips, etc. Such in vitro packing facilitates the surgical procedure because it is often time consuming and relatively difficult, especially for example in cervical applications, to pack the cage in vivo. It would also be advantageous if such insertion tool could be additionally used to insert/position an empty implant for subsequent in vivo packing and closure.

SUMMARY

Apparatus for and methods of inserting implants are disclosed wherein the apparatus includes a handle portion and a body portion attached to the handle portion and defining a longitudinal axis. The body portion includes an outer tubular member fixed relative to the handle portion for rotation therewith about the longitudinal axis. The outer tubular member has first implant engaging structure adjacent a distal end. An inner tubular member is disposed at least partially within the outer tubular member and is mounted for longitudinal motion relative to the outer tubular member. Second implant engaging structure is positioned adjacent a distal end of the inner tubular member. The body portion further includes an inner shaft, coaxially mounted at least partially within the inner tubular member for independent rotation relative to the inner and outer tubular members, the inner shaft having third implant engaging structure adjacent a distal end.

In a method for inserting an implant having a hollow portion with a closed distal end and a removable cap, the first, second and third implant engaging structures are attached to the implant with at least one of the engaging structures attached to the removable cap and another of the engaging structure attached to the hollow portion. The implant is preferably preloaded with bone chips and/or bone growth inducing substances prior to attachment Thereafter, the preloaded implant is inserted into the desired surgical location.

BRIEF DESCRIPTION OF THE DRAWINGS

Various embodiments of the subject implant insertion apparatus are described below with reference to the drawings wherein.

DETAILED DESCRIPTION OF PREFERRED EMBODIMENTS

The preferred embodiments of the apparatus and methods disclosed herein are discussed in terms of orthopedic spinal fusion procedures and apparatus. It is also envisioned, however, that the disclosure is applicable to a wide variety of procedures including, but not limited to ligament repair, joint repair or replacement, non-union fractures, facial reconstruction and spinal stabilization. In addition, it is believed that the present apparatus finds application in both open and minimally invasive procedures including endoscopic and arthroscopic procedures wherein access to the surgical site is achieved through a cannula or small incision.

In the description which follows, the term "proximal", as is traditional, will refer to the portion of the structure which is closer to the operator, while the term "distal" will refer to the portion which is further from the operator.

Figures 1, 2:
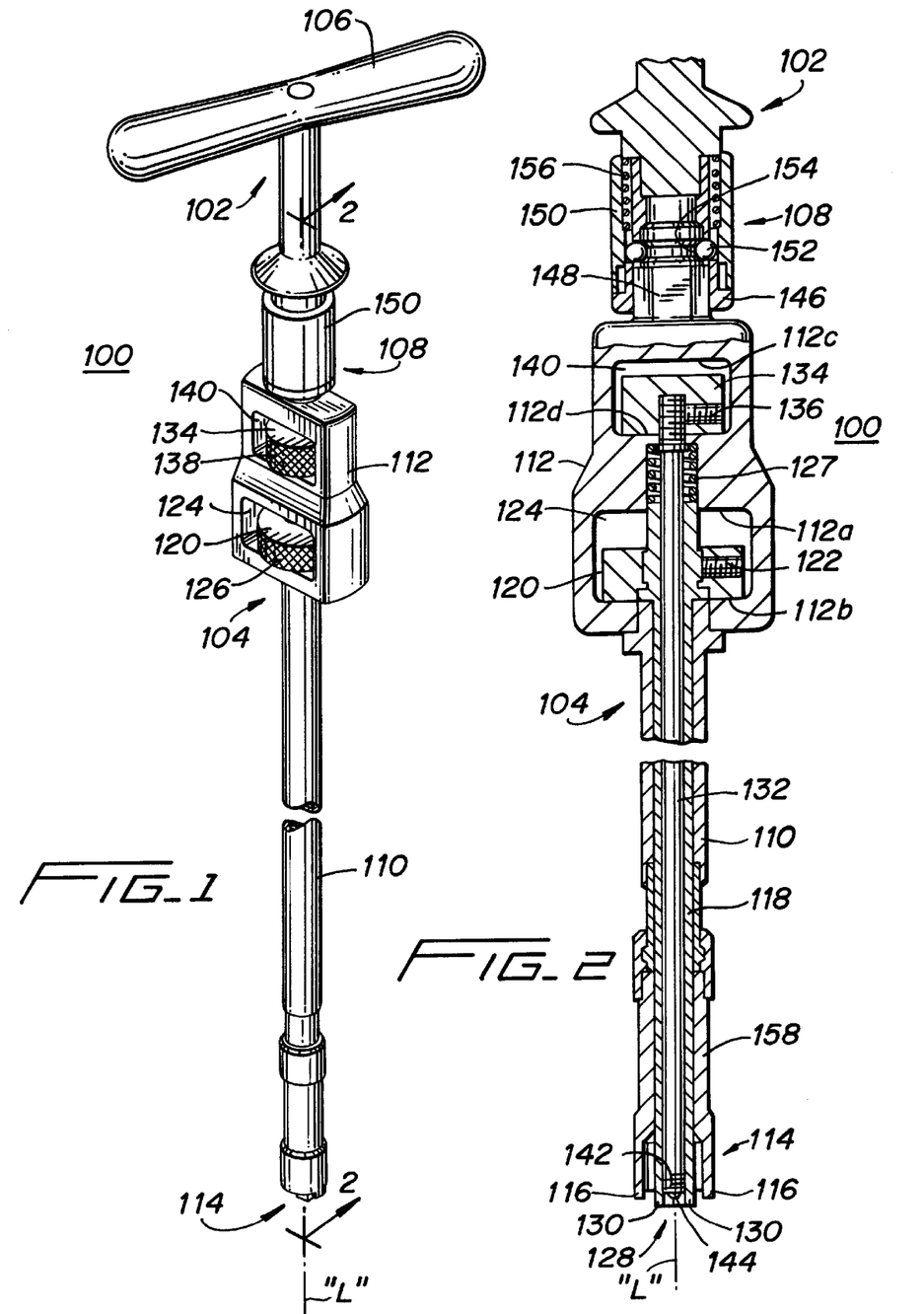
FIG. 1 is a perspective view of an implant insertion apparatus constructed in accordance with a preferred embodiment of the subject disclosure.
FIG. 2 is a side view in cross-section of the implant insertion apparatus taken along line 2—2 of FIG. 1.

Referring now in detail to the drawings in which like reference numerals identify similar or identical elements, a preferred embodiment of the implant insertion apparatus is illustrated in FIGS. 1 and 2 and is designated generally by reference numeral 100. Implant insertion apparatus 100 includes a removable handle portion 102 and a body portion 104. Handle portion 102 has a T-handle 106 positioned at a proximal end and releasable engagement structure 108 at a distal end thereof.

Body portion 104 defines a longitudinal axis "L" and includes an outer tubular member 110 fixed to a housing 112 for longitudinal rotation therewith. First implant engaging structure 114 is positioned adjacent a distal end of outer tubular member 110. Outer tubular member 110 preferably includes a removable distal end portion 158 described below. In the embodiment shown, the implant engaging structure is a pair of distally extending tabs 116 projecting from the distal end of outer tubular member 110.

Body portion 104 further includes an inner tubular member 118 disposed at least partially within outer tubular member 110. Inner tubular member 118 is mounted for limited longitudinal motion relative to outer tubular member 110 and is independently rotatable relative to outer tubular member 110 by wheel 120. In the illustrated embodiment, set screw 122 anchors wheel 120 to the inner tubular member 118. A first cavity 124 is defined in housing 112 and is dimensioned to limit the relative longitudinal motion of inner tubular member 118 by confining wheel 120 between walls 112a, 112b. As shown in FIG. 1, the periphery of wheel 120 may be provided with knurling 126 to enhance its frictional characteristics.

Inner tubular member 118 is normally biased to a distalmost longitudinal position relative to outer tubular member 110 as shown in FIG. 2. Coil spring 127, mounted in housing 112, abuts a proximal end of inner tubular member 118 and biases inner tubular member distally. Second implant engaging structure 128 is formed adjacent a distal end of the inner tubular member 118. In the illustrated embodiment, the second implant engaging structure 128 is a hollow polygonal structure having a plurality of flat sides 130 extending from the distal end of inner tubular member 118.

Body portion 104 also includes an inner shaft 132, coaxially mounted at least partially within the inner tubular member 118. Inner shaft 132 is longitudinally rotatable relative to inner tubular member 118 and outer tubular member 110 by wheel 134. As shown, set screw 136 connects wheel 134 to a distal end of inner shaft 132. In a preferred embodiment, the outer periphery of wheel 134 is provided with a friction enhancing surface such as knurling 138.

A second cavity 140 is defined in housing 112 proximal to first cavity 124 and serves to confine wheel 134, and thus inner shaft 132, to limited longitudinal motion relative to outer and inner tubular members 110 and 118, respectively, between walls 112c, 112d. Wheels 120 and 134 preferably extend radially beyond at least one outer peripheral surface of house 112 to facilitate actuation by the fingers of a user.

Figures 6, 6A:
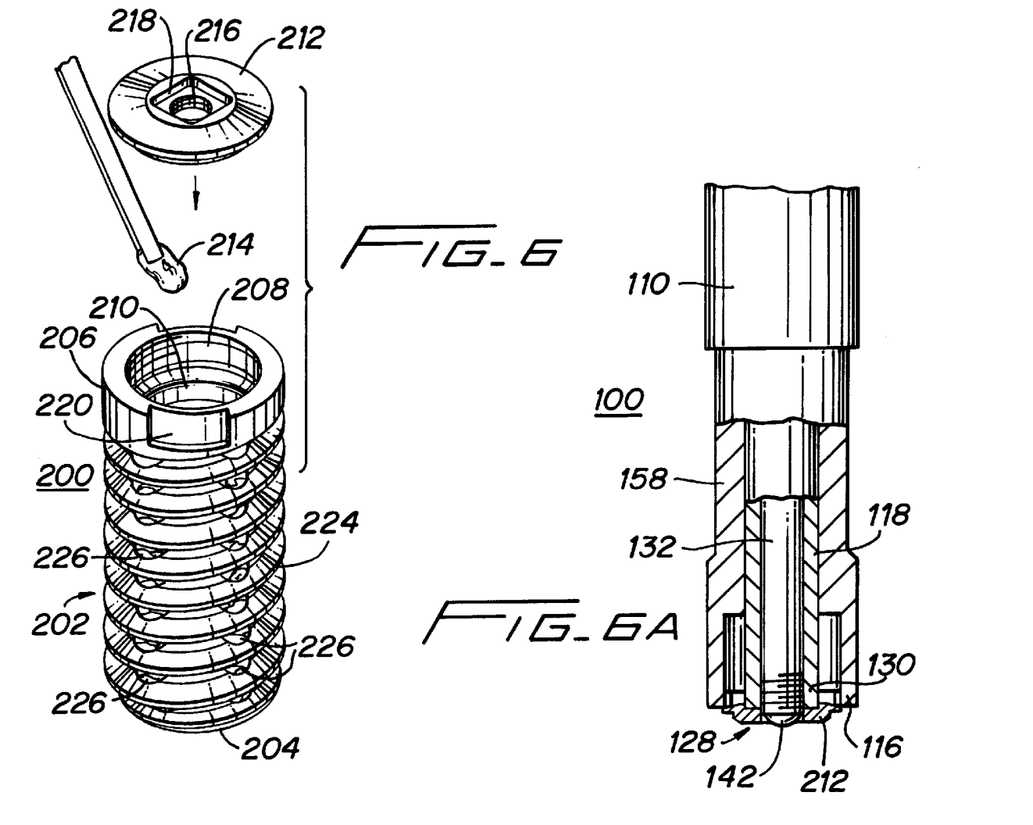
FIG. 6 is an enlarged perspective view of the implant of FIG. 3 with parts separated and loading of bone chips in process.
FIG. 6A is a side view in partial cross-section showing an end cap mounted to the inner tubular member and the inner shaft.

Inner shaft 132 has third implant engaging structure 142 positioned adjacent a distal end (See FIGS. 2 and 6A). In the illustrated embodiment, this structure is threads 144 formed on a distal end of inner shaft 132.

Figure 2A:
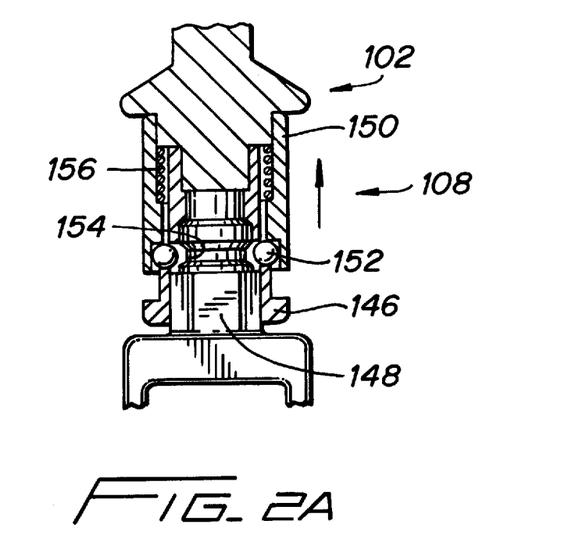
FIG. 2A is an enlarged side view in cross-section of the connection between the handle portion and the body portion of the implant insertion apparatus of FIG. 1.

Referring now to FIGS. 2 and 2A, releasable engagement structure 108 of the illustrated embodiment of implant insertion apparatus 100 includes a distal sleeve 146 having an inner surface configured to engage hexagonal projection 148 formed on a proximal end of housing 112.

Proximal sleeve 150 is operatively associated with distal sleeve 146 and includes an internal spring loaded ball system 152 configured to releasably engage an annular channel 154 which extends proximally from hexagonal projection 148. Proximal sleeve 150 is mounted on a distal end of handle portion 102 for relative longitudinal motion between a locked position (FIG. 2) and an unlocked position (FIG. 2A). In the locked position, ball system 152 is forced radially inward into annular channel 154. Spring 156 normally biases proximal sleeve 150 into this locked position. As shown in FIG. 2A, in the unlocked position, proximal sleeve 150 is retracted to release ball system 152 from annular channel 154. This enables the removal of handle portion 102 from the body portion 104 so the handle portion can be attached to and used with other instrumentation necessary for performing the surgical procedure.

Figure 2B:
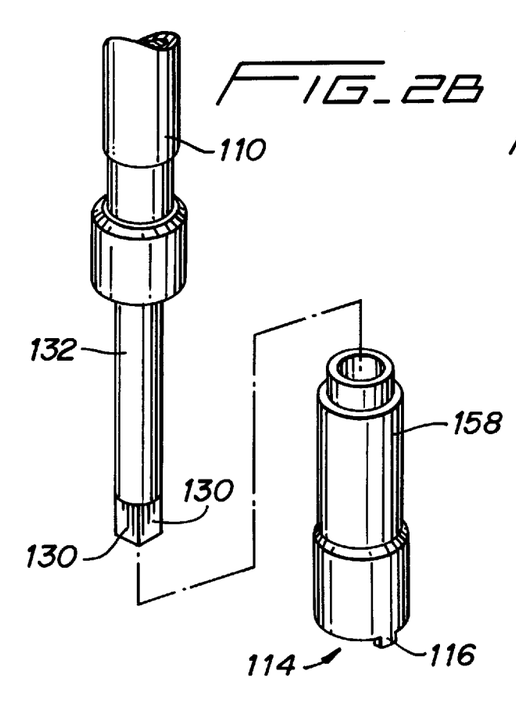
FIG. 2B is an enlarged perspective view of the distal ends of the outer and inner tubular members of the implant insertion apparatus of FIG. 1.
Figure 2C:
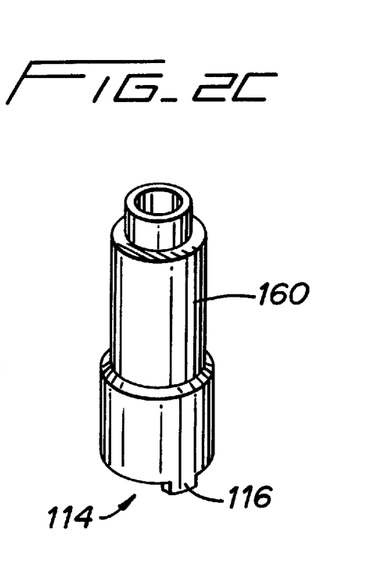
FIG. 2C is an enlarged perspective view of an interchangeable distal end of the outer tubular member of the implant insertion apparatus of FIG. 1.

Referring to FIGS. 2B and 2C in view of FIG. 1, a versatile feature of the illustrated embodiment is shown. In this preferred embodiment, a distal end portion 158 of outer tubular member 110, which contains first implant engagement structure 114, is interchangeably attached via a friction fit. This allows the user to position another distal end portion 160, such as that shown in FIG. 2C, mounting either a different size (e.g. diameter) implant or configuration of implant engagement structure on the same implant insertion apparatus. Thus, the insertion apparatus can be readily adapted to insert different implants.

Figure 3:
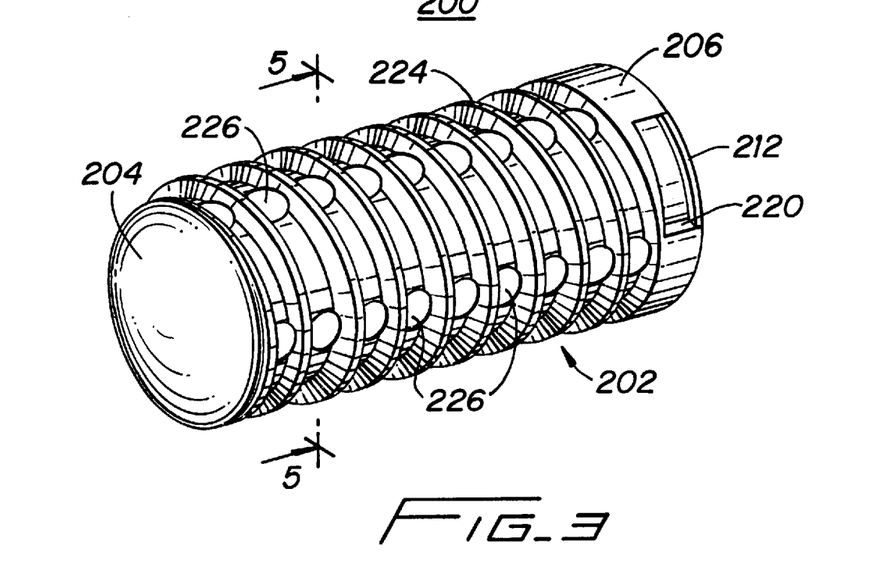
FIG. 3 is an enlarged perspective view of one type of implant configured for interbody fusion.
Figure 4:
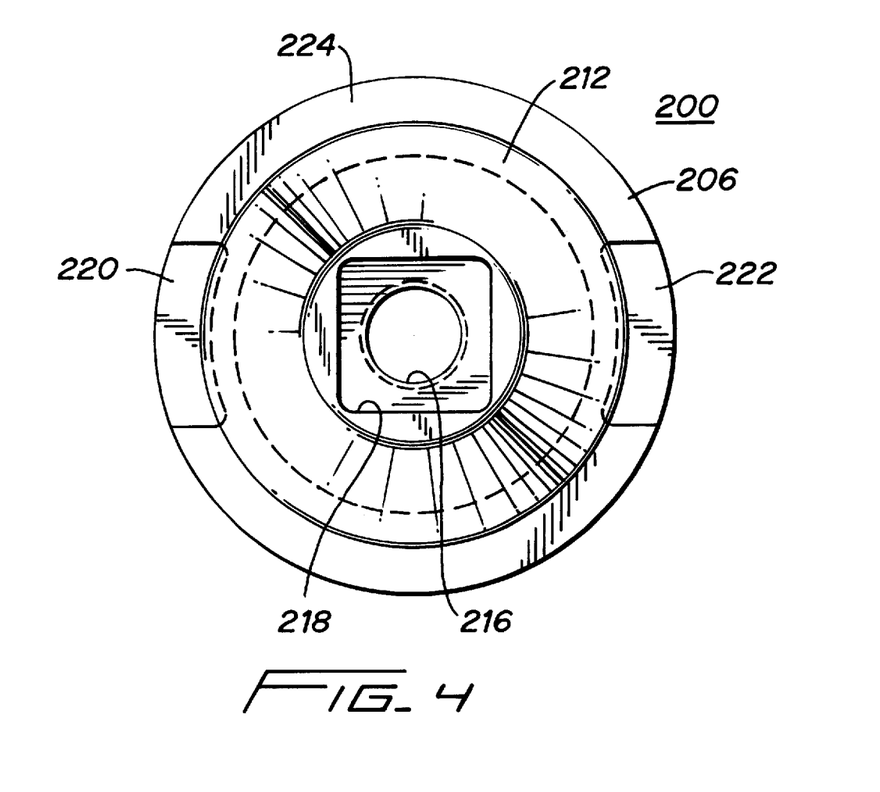
FIG. 4 is an enlarged proximal end view of the implant of FIG. 3 illustrating the structure of the removable end cap.
Figure 5:
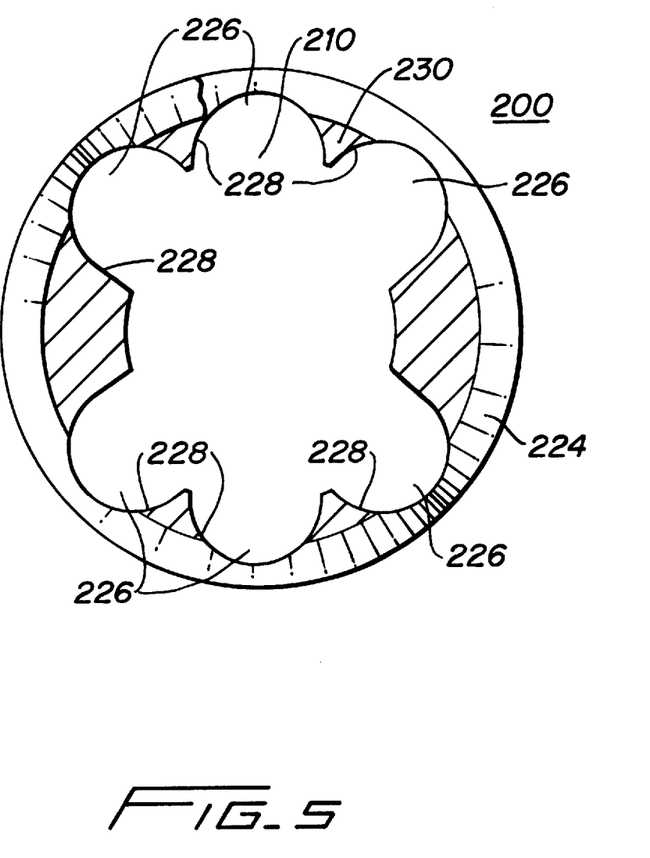
FIG. 5 is an enlarged end view in cross-section of the implant taken along line 5—5 of FIG. 3.

An implant designed for use in spinal fusion procedures is shown in FIGS. 3–5 and designated generally by the reference number 200. This implant is commonly referred to as a "fusion cage" and, in this embodiment, is specifically configured for a posterior access spinal fusion procedure. Subsequent discussion regarding an exemplary use of the implant insertion tool 100 will be focused on this posterior spinal fusion procedure inserting fusion cage 200. It is contemplated, however, that the disclosed implant insertion tool has broad application in a wide variety of implant insertion procedures beyond either anterior or posterior spinal fusion.

Fusion cage 200 includes a body portion 202 with a closed distal end 204 and a proximal end 206. The distal end 204 is rounded or bull nosed to facilitate insertion of the fusion cage 200 relative to one or more bone structures. The proximal end 206 defines an opening 208 (FIG. 6) which communicates with an internal cavity 210 (FIG. 5) defined by fusion cage 200. In the illustrated embodiment, opening 208 is threaded to receive an end cap 212. This end cap 212 is used to close off the proximal end 206 and to retain bone growth inducing substances, such as bone chips 214 (FIG. 6), packed therein.

Referring to FIG. 4, end cap 212 defines a threaded bore 216 which is configured to receive third implant engaging structure 142 of inner shaft 132 as will be discussed in further detail below. End cap 212 also defines a substantially square depression 218 coaxial with thread bore 216 and configured to receive second implant engaging structure 128 on inner tubular member 118.

The proximal end 206 further defines first and second peripheral indentations 220, 222 which are centered about transverse axis "T". These peripheral indentations 220, 222 are configured to receive first implant engagement structure 114, in this case tabs 116. These indentations may also be used to line up the fusion cage 200 for proper insertion and placement between the adjacent vertebral structure.

A helical thread 224 is formed on the outer peripheral surface of the fusion cage 200. A plurality of apertures 226 are defined by and extend through the fusion cage 200. In the illustrated fusion cage 200, apertures 226 are formed by broaching grooves 228 (FIG. 5) in the internal surface 230 of internal cavity 210. This technique removes material from the valleys between the turns of the thread 224, thus defining apertures 226 to advantageously provide immediate contact between the vertebral body and the bone chips located inside the cage when the cage is positioned in the body.

Figure 7:
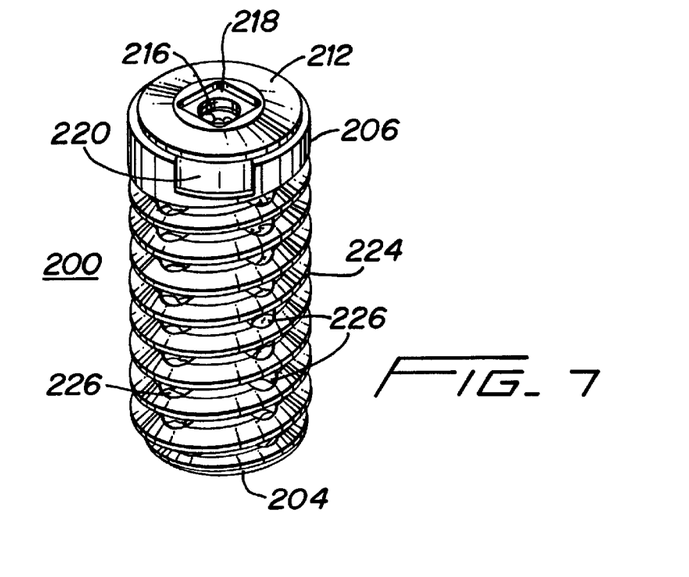
FIG. 7 is a perspective view of a preloaded implant with removable end cap in place.

Referring now to FIGS. 6, 6A and 7, two methods of closing the end cap 212 in the opening 208 of proximal end 206 are illustrated. In FIG. 6, bone chips 214 are deposited into internal cavity 210 using forceps. Thereafter, end cap 212 can be manually threaded into opening 208 either by hand or with a socket wrench-type instrument. Alternatively, end cap 212 can be positioned into engagement with second and third implant engaging structure 128, 142 of implant insertion apparatus 100. This is done by positioning the flat sides 130 of second implant engaging structure 128 into square depression 218 of end cap 212. The distal end of inner shaft 132 is then threaded into bore 216 of end cap 212 by rotating wheel 134 (FIG. 1). End cap 212 is then securely engaged by the second and third implant engaging structure 128, 142. The implant insertion apparatus 100 is positioned with the engaged end cap 212 in juxtaposed axial alignment with opening 208 in proximal end 206 of fusion cage 200. Rotation of wheel 120 threads the end cap 212 into the fusion cage 200. As shown, in both methods, packing of the cage occurs outside the body. This facilitates insertion of bone chips since the chips are individually placed with a forceps and lightly tapped, e.g., compacted, inside the cage. This is especially advantageous where access to the cage once implanted is limited and/or with smaller cages such as in cervical applications.

Figure 8A:
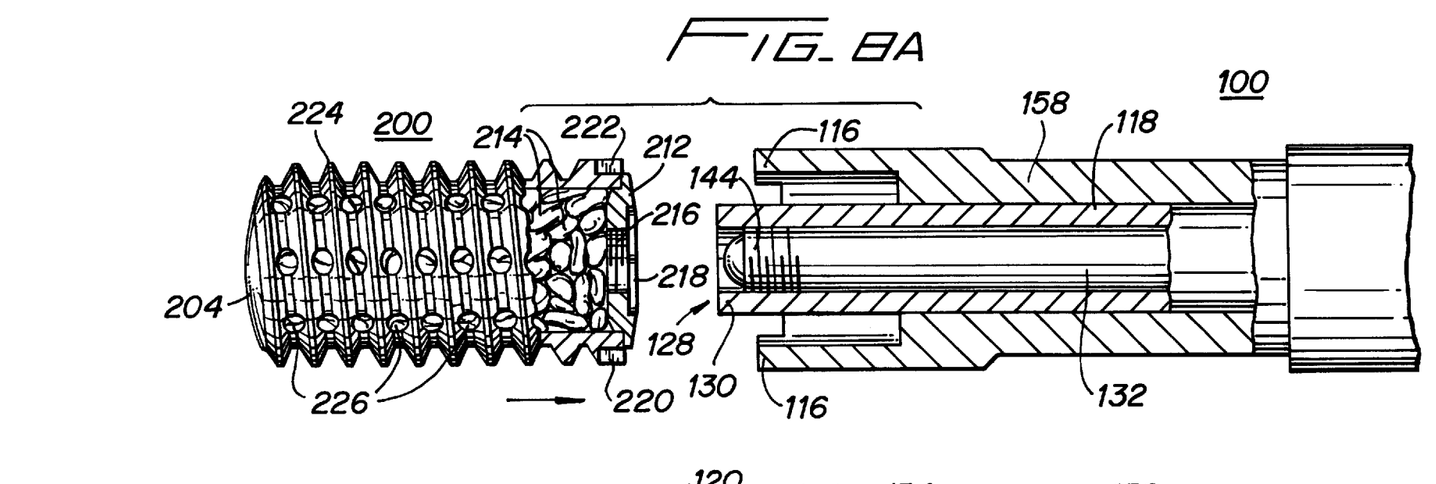
FIG. 8A is an enlarged side view in partial cross-section illustrating the distal end of the implant insertion apparatus of FIG. 1 and the implant of FIG. 7.
Figure 8B:
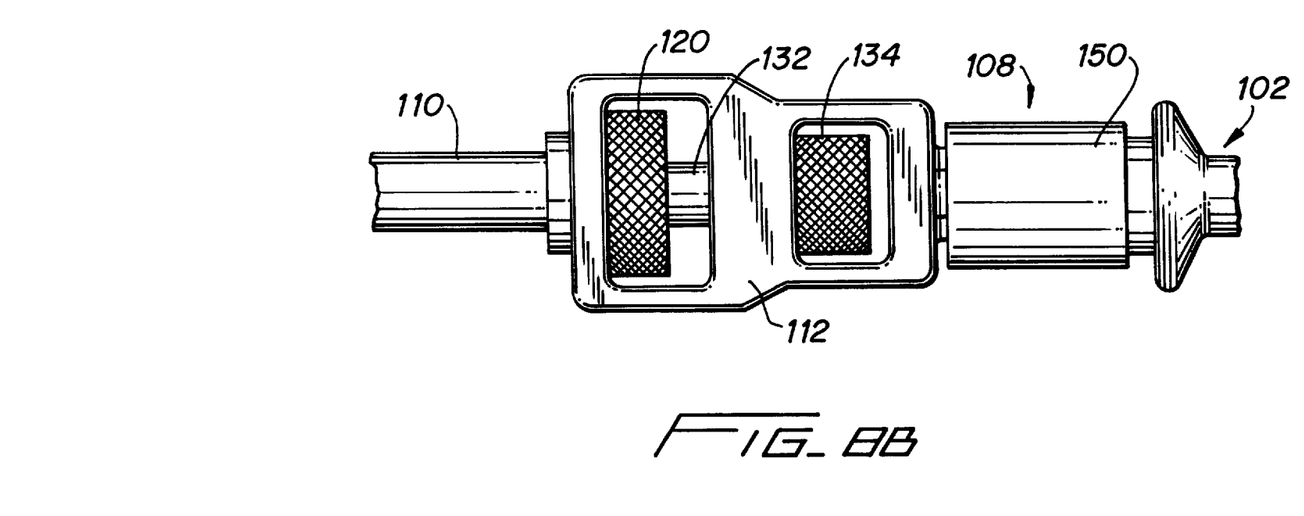
FIG. 8B is an enlarged side view of the housing and rotation wheels of the body portion illustrating the relative position of the inner tubular member as shown in FIG. 8A.
Figure 9A:
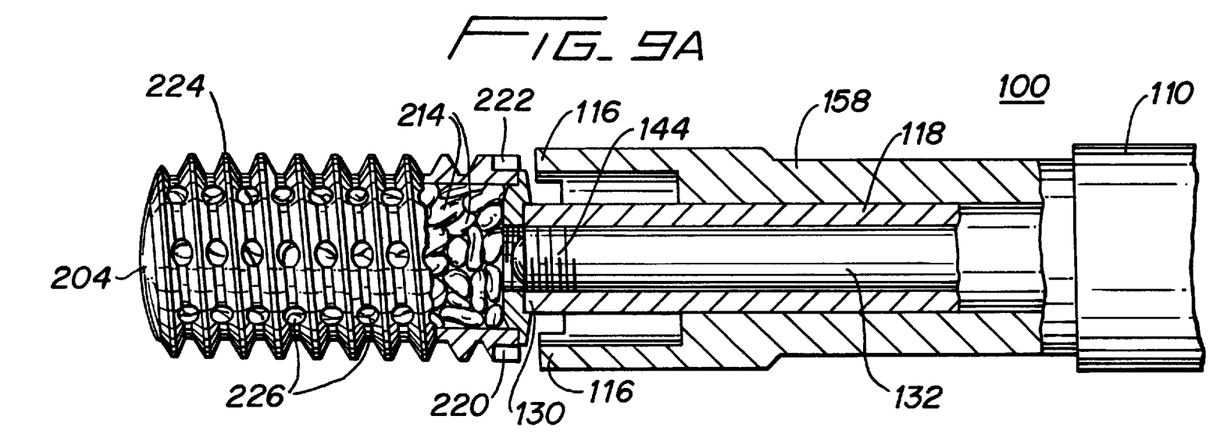
FIG. 9A is an enlarged side view in partial cross-section illustrating the distal end of the implant insertion apparatus of FIG. 1 with the second and third implant engagement structure attached to the removable cap of the implant of FIG. 7.
Figure 9B:
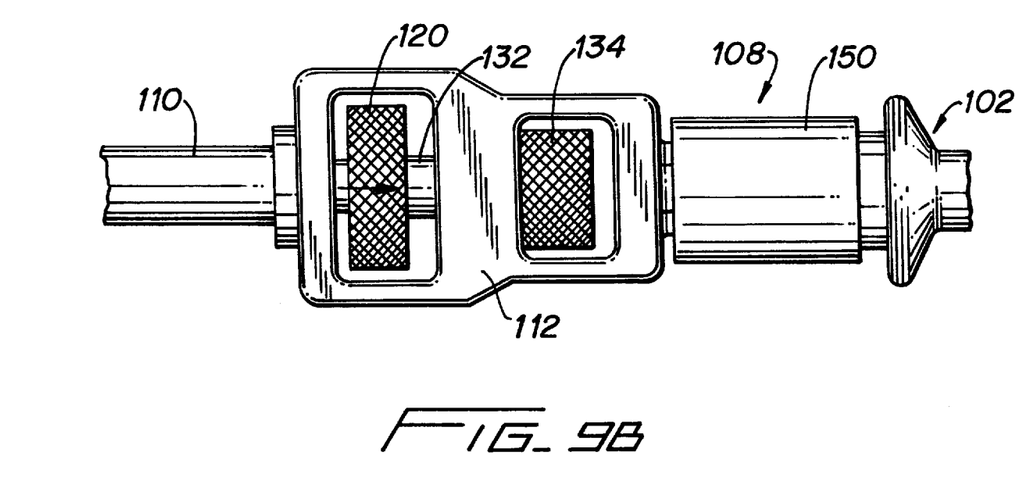
FIG. 9B is an enlarged side view of the housing and rotation wheels of the body portion illustrating the relative position of the inner tubular member and the inner shaft as shown in FIG. 9A.
Figure 10A:
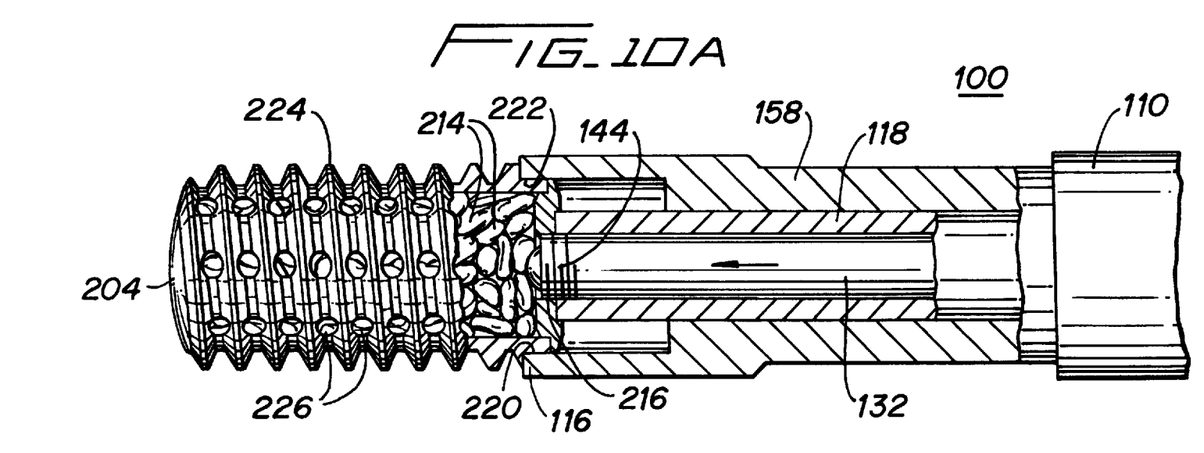
FIG. 10A is an enlarged side view in partial cross-section illustrating the distal end of the implant insertion apparatus of FIG. 1 with the first, second and third implant engagement structure attached to the implant of FIG. 7.
Figure 10B:
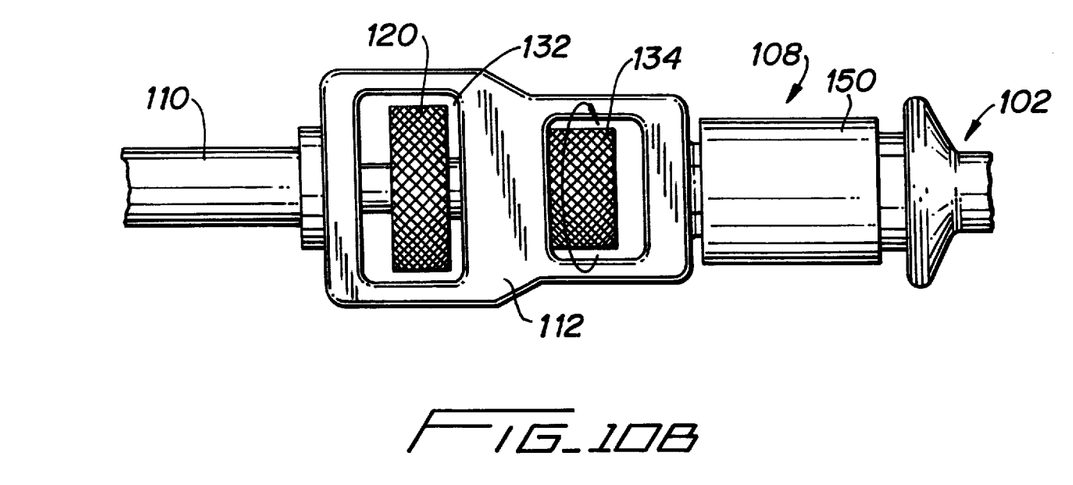
FIG. 10B is an enlarged side view of the housing and rotation wheels of the body portion illustrating the relative position of the inner shaft, the inner tubular member and the outer tubular member as shown in FIG. 10A.

Mounting a packed fusion cage (FIG. 7) onto the insertion apparatus 100 and subsequent insertion into an intervertebral space will now be described with reference to FIGS. 8 through 12. In FIGS. 8A and 8B, the packed fusion cage is positioned in axial alignment with the proximal end of fusion cage 200, aligning tabs 116 with indentations 220, 222; flat sides 130 with square depression 218; and threads 144 with threaded bore 216.

Referring now to FIGS. 9A, 9B, 10A and 10B, fusion cage 200 is moved initially into engagement with inner tubular member 118 such that flat sides 130 are disposed in square depression 218 of end cap 212. Further proximal motion (indicated by the arrows in FIGS. 9A and 9B) of inner shaft 118 relative to inner shaft 132 by either pressing cage 200 against the apparatus or moving wheel 120 proximally brings threads 144 into engagement with threaded bore 216 and tabs 116 of outer tubular member 110 into simultaneous engagement with indentations 220 and 222. (FIG. 10A) Wheel 120 can be slightly rotated to ensure alignment of tabs 116 and indentations 220, 222. Then, wheel 134 is rotated to cause the threaded inner shaft to engage the fusion cage 200 by end cap 212 thus securely mounting the fusion cage 200 on the distal end of the implant insertion apparatus 100 as the cage 200 is pulled proximally via the engagement of the threads.

Figure 11:
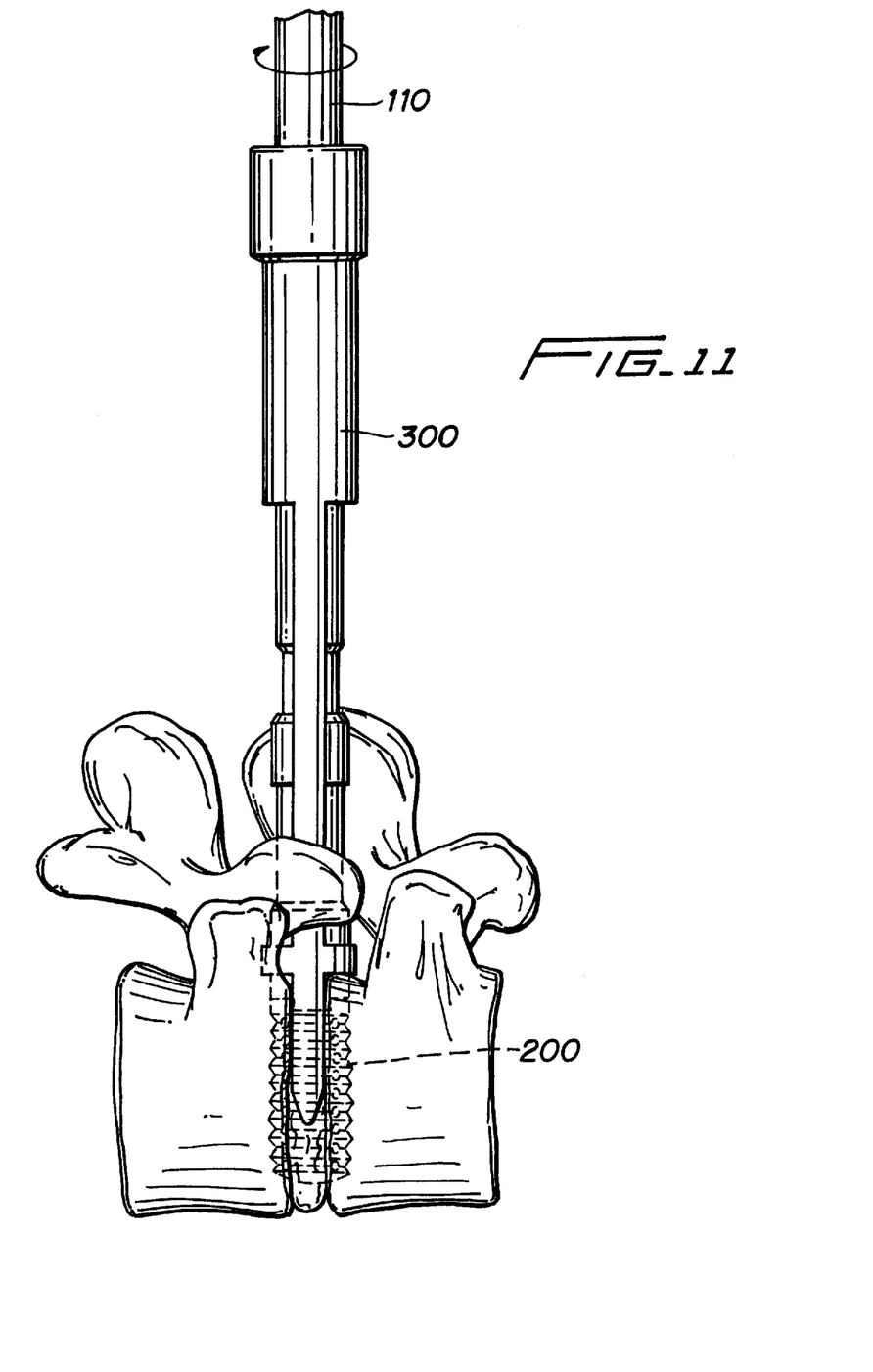
FIG. 11 is a side view illustrating the insertion of the implant of FIG. 7 using the insertion apparatus of FIG. 1.

Thereafter, the implant insertion apparatus 100 is positioned adjacent the implant site (FIG. 11) which typically includes a pretapped bore formed in an intervertebral space between two adjacent vertebra. (Alternately, the fusion cage could be self-tapping.) The implant insertion apparatus 100 may be guided into position using a cannula or C-retractor 300 to facilitate accurate insertion of fusion cage 200. The T-handle 106 is then rotated to rotate outer tubular member 110 to engage threads 224 of the fusion cage 200 (shown in phantom) in the intervertebral space 302.

Figure 12:
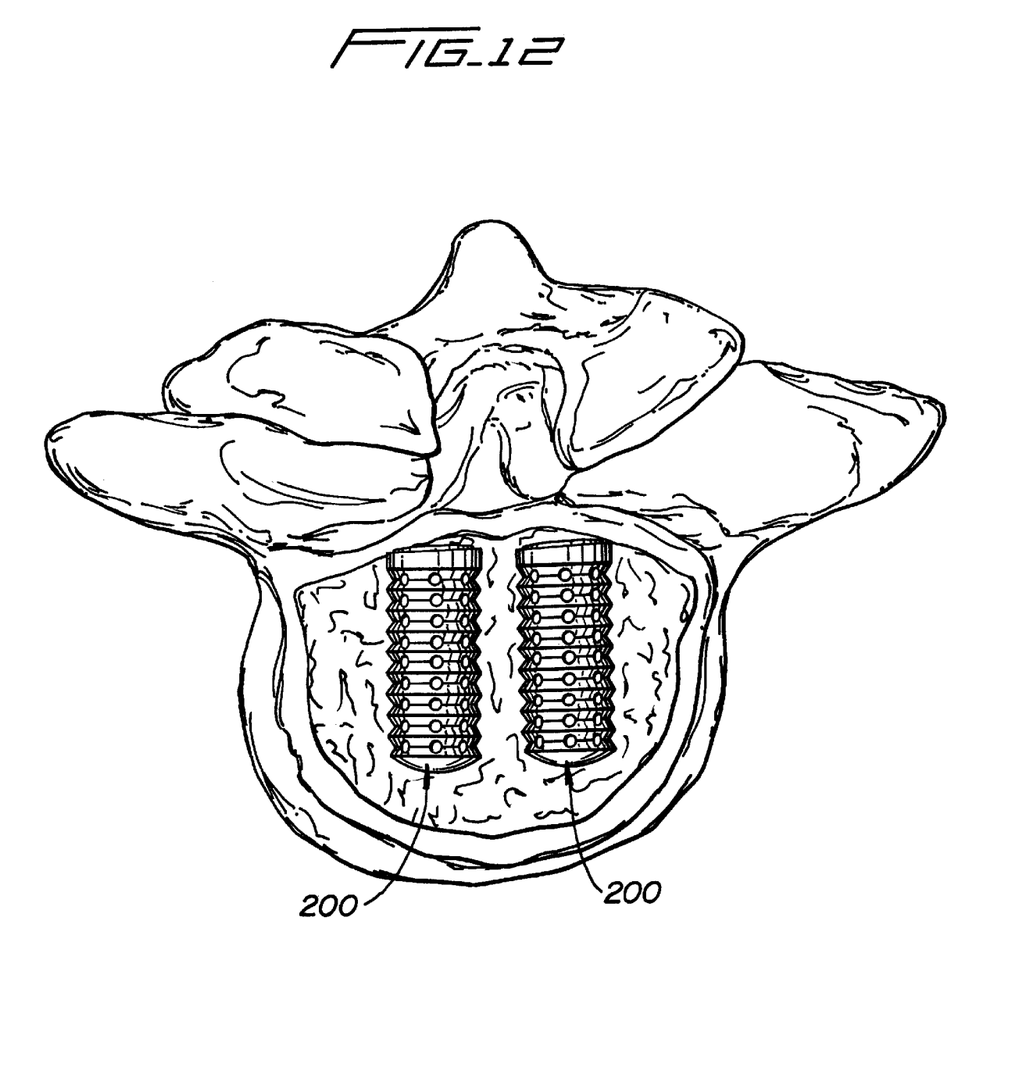
FIG. 12 is an enlarged top view in partial cross-section of a pair of implants in place in the intervertebral space of a lumbar spinal section.

Once the fusion cage 200 is in position, wheel 134 is rotated to disengage threads 144 from threaded bore 216. This releases the implant insertion apparatus 100 from the implanted fusion cage 200. (FIG. 12)

Note that since the fusion cage 200 is grasped and inserted by the apparatus 100 from its open end, once positioned inside the body, the end cap 212 can be removed if the user desires to view or access the bone chips in the internal cavity 210.

The implant insertion apparatus 100 can also be utilized to insert an empty implant such as fusion cage 200 into the intervertebra space and subsequently seal the fusion cage after packing the fusion cage with bone growth inducing substance in vivo. In this procedure, the empty fusion cage is engaged with the first, second and third implant engagement structure 114, 128, 142 and inserted in the same manner outlined above. Once in place in the body, wheel 120 is rotated to remove end cap 212 from body portion 202 and the implant insertion apparatus with attached end cap 212 (FIG. 6A) is removed from the site.

Thereafter, the fusion cage 200 can be packed and the procedure reversed to thread the end cap 212 securely back into place on the body portion 202 using apparatus 100 as described above without affecting the relative position of the body portion 202 at the site. This would avoid the necessity for a separate cap insertion tool since apparatus 100 could serve the dual function of inserting the cage and attaching the end cap.

It will be understood that a wide variety of modifications may be made to the embodiments of the apparatus and methods disclosed herein. For example, the first, second and/or third implant engaging structures can be modified to facilitate engagement with a vast number of implants, both prosthetic and natural. Also, endoscopic, arthroscopic and percutaneous methods of use are easily accommodated. Therefore, the above description should not be construed as limiting, but merely as exemplifications of preferred embodiments. Those skilled in the art will envision other modifications within the scope and spirit of the claims appended hereto.

What is claimed is:

1. Apparatus for implant insertion comprising:
   a housing portion;
   a body portion attached to the housing portion and defining a longitudinal axis, the body portion including:
      an outer member mounted to the housing portion, the outer member having first implant engaging structure adjacent a distal end thereof;
      an inner member mounted within the outer member and being rotatable independent of the outer member, the inner member having second implant engaging structure adjacent a distal end thereof;
      an inner shaft coaxially mounted at least partially within the inner member for independent rotation relative to the inner and outer members, the inner shaft having third implant engaging structure adjacent a distal end thereof; and
   a first actuator mounted adjacent the housing and operatively connected to the inner member, the first actuator movable to cause corresponding longitudinal movement of the inner member; and
   a second actuator mounted adjacent the housing and operatively connected to the inner shaft, the second actuator movable to cause corresponding rotational movement of the inner shaft.

2. Apparatus as in claim 1 including a handle portion releasably attached to one of the housing portion and the body portion.

3. Apparatus as in claim 2 wherein the handle portion is T-shaped.

4. Apparatus as in claim 1 wherein the first actuator includes a wheel positioned on the inner member for independent rotation thereof relative to the outer member.

5. Apparatus as in claim 1 wherein the second actuator includes a wheel positioned on the inner shaft for independent rotation thereof relative to the outer and inner members.

6. Apparatus as in claim 1 wherein the first implant engaging structure comprises a pair of tabs projecting from the distal end of the outer member.

7. Apparatus as in claim 1 wherein the second implant engaging structure comprises a polygonal structure extending from the distal end of the inner member.

8. Apparatus as in claim 1 wherein the third implant engaging structure comprises a threaded portion formed on the distal end of the inner shaft.

9. Apparatus as in claim 1 wherein the first implant engaging structure is removably mounted to the outer member.

10. Apparatus for implant insertion comprising:
    a handle portion; and
    a body portion defining a longitudinal axis and having a proximal end configured to engage the handle portion, a distal end configured to engage an implant, and a housing fixed relative to the proximal end and positioned intermediate the proximal and distal ends, the body portion including an outer tubular member fixed to the housing and extending distally therefrom, the outer tubular member having first implant engaging structure at a distal end, an inner tubular member disposed at least partially within the outer tubular member and mounted for longitudinal motion relative to the outer tubular member, the inner tubular member including a first wheel confined at least partially within a first cavity in the housing for rotating the inner tubular member relative to the outer tubular member, the inner tubular member having second implant engaging structure adjacent a distal end and an inner shaft, coaxially mounted at least partially within the inner tubular member, the inner shaft including a second wheel confined at least partially within a second cavity in the housing for independently rotating the inner shaft relative to the inner and outer tubular members, the inner shaft having third implant engaging structure adjacent a distal end.

11. Apparatus as in claim 10 wherein the first implant engaging structure comprises a pair of tabs projecting from the distal end of the outer tubular member.

12. Apparatus as in claim 11 wherein the tabs are on radially opposed sides of the longitudinal axis and are configured to engage an outer peripheral wall of an implant.

13. Apparatus as in claim 10 wherein the second implant engaging structure comprises a polygonal structure extending from the distal end of the inner tubular member.

14. Apparatus as in claim 10 wherein the third implant engaging structure comprises a threaded portion formed on the distal end of the inner shaft.

15. Apparatus as in claim 10 wherein the first implant engaging structure is removably mounted to the body portion.

16. Apparatus as in claim 10 wherein the handle portion is T-shaped.

17. An apparatus for facilitating placement of an intervertebral implant, which comprises:

a housing;

an elongated body portion connected to the housing and extending at least distally therefrom, the elongated body including:

an outer member fixedly mounted to the housing and having first implant engaging structure at a distal end thereof;

an inner member disposed at least partially within the outer member and having second implant engaging structure at a distal end thereof, the inner member mounted for rotational and longitudinal movement relative to the outer member;

a shaft member at least partially disposed within the inner member and having third implant engaging structure at a distal end thereof, the shaft member mounted for rotational movement relative to the inner member;

a first manually rotatable member mounted adjacent the housing and operatively connected to the inner member, the first rotatable member being rotatable and longitudinally movable relative to the housing to cause corresponding respective rotational and longitudinal movement of the inner member relative to the outer member; and a second manually rotatable member mounted adjacent the housing and operatively connected to the shaft member, the second rotatable member being rotatable relative to the housing to cause corresponding rotational movement of the shaft member.

18. Apparatus as in claim 17 wherein the first implant engaging structure includes a projecting member extending from the distal end of the outer member.

19. Apparatus as in claim 18 wherein the first implant engaging structure includes a pair of opposed projecting members extending from the distal end of the outer member.

20. Apparatus as in claim 17 wherein the second implant engaging structure includes a polygonal member extending from the distal end of the inner member.

21. Apparatus as in claim 17 wherein the third implant engaging structure includes a threaded potion disposed on the distal end of the shaft member.

22. Apparatus as in claim 17 wherein the second rotatable member is mounted for longitudinal movement relative to the housing portion to cause corresponding longitudinal movement of the shaft member.

23. A system for facilitating fusion of adjacent vertebrae, which comprises:

an implant including an implant body defining leading and trailing ends, and an end cap mountable to the trailing end of the implant body, the implant body having at least one recess adjacent the trailing end, the end cap defining an indenture in an outer surface thereof and an internally threaded bore; and an insertion tool for facilitating positioning of the implant within the adjacent vertebrae, the insertion tool, including:

an elongated body defining a longitudinal axis and having proximal and distal ends, the elongated body including:

an outer member having at least one tab extending from a distal end of the outer member, the tab being dimensioned to be accommodated within the recess of the implant body;

an inner member at least partially disposed within the outer member, the inner member having projecting structure extending from a distal end of the inner member, the projecting structure being dimensioned to be received within the indenture of the end cap of the implant;

an inner shaft at least partially disposed within the inner member and having a threaded portion adjacent a distal end thereof, the threaded portion dimensioned to threadably engage the threaded bore of the end cap of the implant;

wherein the tab, projecting structure and the threaded portion of the insertion tool cooperatively engage the respective recess, indenture and threaded bore of the implant to releasably engage the implant to the insertion tool to thereby facilitate placement of the implant within the adjacent vertebrae.

24. The system as in claim 23 wherein the insertion tool includes a housing mounted to the elongated body.

25. The system as in claim 24 further including a first actuator operatively connected to the inner member and mounted with respect to the housing, the first actuator mounted for longitudinal movement relative to the housing to at least retract the inner member to cause release of the projecting structure from the indenture of the end cap.

26. The system as in claim 25 wherein the first actuator is rotatably mounted relative to the housing to facilitate alignment of the projecting structure of the inner member with the indenture of the end cap.

27. The system as in claim 26 including a second actuator connected to the inner shaft and rotatably mounted with respect to the housing, the second actuator rotatable to cause corresponding rotation of the inner shaft to thereby cause selective engagement of the threaded portion of the inner shaft with the threaded bore of the end cap.

28. The system as in claim 27 including a handle operatively connected to the outer member to facilitate rotation of the outer member and the implant to thereby enhance positioning of the implant with respect to the adjacent vertebrae.

* * * * *